United States Patent [19]

Britcher et al.

[11] Patent Number: 4,772,622

[45] Date of Patent: Sep. 20, 1988

[54] 3,5-DIAMINO-1,2,4-OXIDIAZOLES AS GASTRIC SECRETION INHIBITORS

[75] Inventors: Susan F. Britcher, Norristown; William C. Lumma, Jr., Pennsburg, both of Pa.

[73] Assignee: Merck & Co., Inc., Rahway, N.J.

[21] Appl. No.: 874,757

[22] Filed: Jun. 16, 1986

Related U.S. Application Data

[63] Continuation-in-part of Ser. No. 479,045, Mar. 25, 1983, abandoned, which is a continuation of Ser. No. 472,549, Mar. 7, 1983, abandoned.

[51] Int. Cl.$^4$ .................. A61K 31/41; A61K 31/535; C07D 271/06; C07D 413/02
[52] U.S. Cl. ...................... 514/364; 514/252; 514/253; 514/256; 514/257; 514/318; 514/320; 514/326; 514/333; 514/334; 514/341; 514/362; 514/363; 514/227.8; 514/236.2; 544/60; 544/62; 544/111; 544/114; 544/122; 544/132; 544/295; 544/333; 544/357; 544/360; 544/367; 544/376; 544/405; 546/193; 546/196; 546/277; 546/283; 546/405; 548/127; 548/128; 548/131; 548/133
[58] Field of Search ............... 548/127, 128, 133, 131; 514/362, 363, 364

[56] References Cited

U.S. PATENT DOCUMENTS

| | | | |
|---|---|---|---|
| 3,574,222 | 4/1971 | Eloy et al. | 546/209 |
| 3,950,333 | 4/1976 | Durant et al. | 424/272 |
| 4,089,966 | 5/1978 | Cohen | 514/364 |
| 4,128,658 | 5/1978 | Price et al. | 546/209 |
| 4,394,508 | 7/1983 | Crenshaw | 546/209 |

FOREIGN PATENT DOCUMENTS

| | | |
|---|---|---|
| 3640 | 8/1979 | European Pat. Off. . |
| 6286 | 1/1980 | European Pat. Off. . |
| 10418 | 4/1980 | European Pat. Off. . |
| 14057 | 8/1980 | European Pat. Off. . |
| 1445409 | 5/1976 | Fed. Rep. of Germany . |
| 2023133 | 12/1979 | United Kingdom . |

*Primary Examiner*—Donald G. Daus
*Assistant Examiner*—Cecilia Shen
*Attorney, Agent, or Firm*—R. D. Meredith; H. J. Pfeiffer

[57] ABSTRACT

Novel diamino oxadiazoles, wherein one of the amine functions is connected to a basicly-substituted heterocyclic group through a linear or cyclic connecting group, which are useful for the suppression of gastric acid secretions in mammals. Compositions employing these compounds and processes for the preparation of such compounds from known N-cyano-S-methylisothiourea precursors by treatment with hydroxylamine and for alkylation of amine groups are also disclosed.

20 Claims, No Drawings

3,5-DIAMINO-1,2,4-OXIDIAZOLES AS GASTRIC SECRETION INHIBITORS

BACKGROUND OF THE INVENTION

This application is a continuation-in-part of application Ser. No. 479,045, filed Mar. 25, 1983, now abandoned which is a continuation of application Ser. No. 472,549, filed Mar. 7, 1983, now abandoned.

Compounds containing a heterocycle connected to a cyanoguanidine moiety through a linear or cyclic connecting group are known in the art as H₂ histamine receptor inhibitors and active compounds for the suppression of gastric acid secretions. See, for example, U.S. Pat. No. 3,950,333 to Durant et al, U.S. Pat. No. 4,128,658 to Price et al and European Pat. No. 3640 to Jones et al. In preparing the cyanoguanidine end group, the precursor thereof is an N-cyano-S-methylisothiourea group, which is reacted with the appropriate amine to prepare the described compounds. Applicants have found that the N-cyano-S-methylisothiourea precursor, when reacted with hydroxylamine, produces a compound with an amino-oxadiazole end group.

Belgian Pat. No. 875,846 as abstracted in 20 Derwent Abstract 79110B/44 discloses compounds wherein a triazolyl heterocyclic ring is incorporated into compounds similar to those disclosed in Durant et al, Price et al and Jones et al in place of the guanidino end group. Such compounds do not suggest, however, the instant oxadiazolyl compounds. The instant oxadiazolyl compounds have been found to possess considerable activity in the suppression of gastric acid secretions.

SUMMARY OF THE INVENTION

This invention is concerned with diaminooxadiazole compounds which have one of the amino groups connected to an aminoalkyl heterocyclic moiety through a linear or cyclic connecting group. Thus, it is an object of this invention to describe such compounds. It is a further object of this invention to describe processes for the preparation of such compounds from the appropriately-substituted N-cyano-S-methylisothiourea compound. A still further object is to describe the use of such compounds as gastric secretion-inhibitors in mammals. Further objects will become apparent from a reading of the following description.

DESCRIPTION OF THE INVENTION

The compounds of this invention are best described in the following structural formulae:

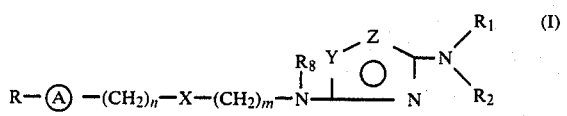

and

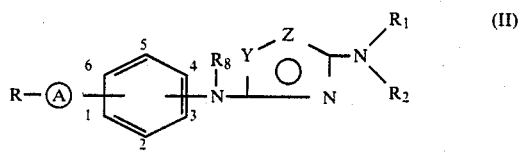

wherein in both of the above structural formulae:
R is hydrogen, loweralkyl,

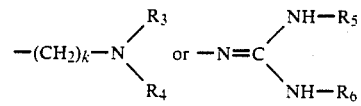

wherein
R₃ and R₄ are independently hydrogen, lower-alkyl, cycloloweralkyl or phenylloweralkyl or R₃ and R₄ may be joined to form, along with the nitrogen to which they are attached, a nonaromatic one- or two-heteroatom-5- or 6-membered heterocycle, the heteroatom of the one-heteroatom-5- or 6-membered heterocycle being said nitrogen atom, and the heteroatoms of the two-heteroatom-5- or 6-membered heterocycle consisting of said nitrogen atom and one member of the group consisting of an oxygen atom, a sulfur atom, and an N—R₇ group, wherein R₇ is hydrogen, loweralkyl of from 1-to-3 carbon atoms or benzyl, and preferably where this 5- or 6-membered nonaromatic heterocycle is selected from pyrolidino, piperidino, thiomorpholino, morpholino, and N-loweralkylpiperazino;
R₅ and R₆ are independently hydrogen or loweralkyl;
n is 0 or 1;
m is 2-to-4;
k is 1-to-4;
X is oxygen, sulfur or methylene;
Y and Z are different, and are either oxygen or nitrogen;
R₁ and R₂ are independently hydrogen; loweralkyl; substituted loweralkyl, where the substituent is phenyl, pyridyl or imidazolyl; loweralkenyl; loweralkynyl; or loweralkanoyl;
R₈ is hydrogen or loweralkyl; and
Ⓐ is phenylene or a 5- or 6-membered aromatic heterocycle consisting of one-to-three heteroatoms in addition to the carbon atoms in the ring, which may optionally have a benzo ring fused thereon, and wherein each heteroatom is selected from oxygen, sulfur and nitrogen;
provided that when Ⓐ in Formula I above is a 5-membered heterocycle or a benzo-fused 5-membered heterocycle, n is 1, and physiologically-acceptable salts thereof.

Ⓐ in the foregoing formulae may be furan, thiophene, pyrrole, oxazole, oxadiazole, thiadiazole, thiazole, triazole, pyrazole, imidazole, pyridine, pyrimidine, pyrazine, and the like, and the fused benzo derivatives thereof may be benzofuran, benzoxazole, benzimidazole, and the like.

In the instant invention, unless specified otherwise, the term "loweralkyl" is intended to include those alkyl groups containing from 1-to-5 carbon atoms in either a straight or branched configuration. Examples of such alkyl groups include methyl, ethyl, propyl, iso-propyl, butyl, sec-butyl, pentyl and the like. By "substituted loweralkyl" is meant a "loweralkyl" substituted by a phenyl, pyridyl or imidazolyl group.

The term "cycloloweralkyl" is intended to include those cycloalkyl groups of from 3-to-7 carbon atoms. Examples of such cycloalkyl groups include cyclopropyl, cyclobutyl, cyclopentyl, cyclohexyl, and cycloheptyl.

The term "loweralkenyl" is intended to include those alkenyl groups of 2-to-5 carbon atoms of either a straight or branched configuration and one unsaturation. Examples of such alkenyl groups are ethenyl, propenyl, butenyl, pentenyl, and the like.

The term "loweralkanoyl" is intended to include those alkyl-carbonyl groups of from 1-to-5 carbon atoms. Examples of such alkanoyl groups included formal, acetyl, propanoyl and butanoyl.

The term "loweralkynyl" is intended to include those alkynyl groups of from 2-to-5 carbon atoms of either a straight or branched configuration, and one triple bond. Examples of such alkynyl groups are ethynyl, propargyl, butynyl, pentynyl and the like.

The term "heterocycle" is intended to include ring structures of a specified number of ring members consisting of carbon atoms and a specified number of "heteroatoms", which are specified as selected from among the members of the group consisting of O, S, N and $NR_7$, as defined at each particular occurrence.

The preferred compounds according to the present invention include those wherein $R_1$ and $R_2$ are independently hydrogen, $C_1$- or $C_2$-alkyl or $C_2$- or $C_3$-alkynyl, $R^8$ is hydrogen and in the compounds of Formula I, m is 2 or 3 and X is O or S, and in those of Formula II, 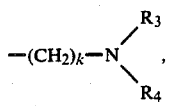 is connected to the phenyl ring at the 1 position and the phenyl ring is connected to the nitrogen (which is also connected to $R_8$) from the 3 position. Particularly, these compounds include those wherein 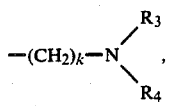 is phenylene and R is $$-(CH_2)_k-N\begin{matrix}R_3\\ \\R_4\end{matrix},$$

where k is one, and $R_3$ and $R_4$ are independently hydrogen or $C_1$-$C_5$-alkyl or $R_3$ and $R_4$ are joined with the nitrogen to which they are attached to form piperidino or morpholino, and in Formula I compounds, X is oxygen, m is three, and n is zero, and those wherein 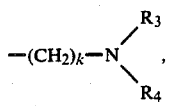 is an aromatic one-heteroatom 5-membered heterocycle, the single heteroatom of which is an oxygen atom or a sulfur atom, or a benzofused one-heteroatom-5-membered-heterocycle, the single heteroatom of which is an oxygen atom or a sulfur atom, and R is $$-(CH_2)_k-N\begin{matrix}R_3\\ \\R_4\end{matrix},$$

where k is one, and $R_4$ are independently hydrogen or $C_1$-$C_5$-alkyl or $R_3$ and $R_4$ are joined with the nitrogen to which they are attached to form a nonaromatic one-heteroatom-5- or 6-membered heterocycle, and in Formula I compounds, X is sulfur, m is two, and n is one. These compounds also include those wherein 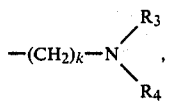 is an aromatic two-heteroatom-5-membered-heterocycle, one heteroatom of which is nitrogen, and R is

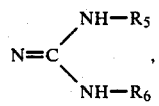

and in Formula I compounds, X is sulfur, m is two, and n is one, and those wherein 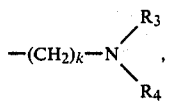 is an aromatic three-heteroatom-5-membered-heterocycle, at least one heteroatom of which is nitrogen, and R is

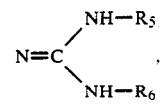

and in Formula I compounds, X is sulfur, m is two, and n is one. Still other preferred compounds are those wherein 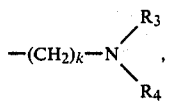 is an aromatic two-heteroatom-5-membered heterocycle, the two heteroatoms of which are nitrogen atoms, R is hydrogen or methyl, and in Formula I compounds, X is sulfur, m is two, and n is one.

The compounds according to the invention readily form physiologically-acceptable salts. Such salts include salts with inorganic acids such as hydrochlorides, hydrobromides, sulfates, nitrates and phosphates. Particularly useful salts of organic acids are formed with aliphatic mono- or dicarboxylic acids. Examples of such salts include acetates, maleates fumarates, tartrates, citrates, benzoates, succinates and isothenates. The compounds and their salts may also form hydrates and solvates. In addition, the nitrogen atoms in groups R, 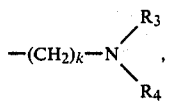, $R_1$ and $R_2$ may also form quaternary salts and N-oxides.

As stated above, the compounds represented by Formula I have been found to have pharmacological activity in the animal body as antagonists to certain actions of histamine which are not blocked by "antihistamines" such as mepyramine. For example, they have been found to inhibit selectively the histamine-stimulated secretion of gastric acid from in the stomach of chronic fistula dogs at doses of from 0.001 to 5 mg per kilogram intravenously, or orally from 0.01 to 10 mg per kilogram. Similarly, the action of these compounds is demonstrated by their antagonism to the effects of histamine on other tissues which are not affected by histamine H1 antagonists. An example of such tissue is the isolated guinea-pig right atrium. The compounds of the invention have also been found to inhibit the secretion of gastric acid stimulated by pentagastrin or by food.

The pharmaceutical carrier employed may be, for example, either a solid or liquid, such as, for solids, lactose, terra alba, sucrose, talc, gelatin, agar, pectin, acacia, magnesium stearate, stearic acid and the like, and for liquids, syrup, peanut oil, olive oil, water and the like.

A wide variety of pharmaceutical forms may be employed. Thus, if a solid carrier is used, the preparation may be tableted, placed in a hard gelatin capsule in powder or pellet form, or in the form of a troche or lozenge. The amount of solid carrier will vary widely but preferably will be from about 15 mg to about 0.4 gm. If a liquid carrier is used, the preparation may be in the form of a syrup, emulsion, soft gelatin capsule, sterile injectable liquid such as an ampoule, or an aqueous of nonaqueous liquid suspension.

The pharmaceutical compositions are prepared by conventional techniques involving procedures such as mixing, granulating and compressing or dissolving the ingredients as appropriate to the desired preparation.

The active ingredient will be present in the composition in an effective amount to inhibit histamine activity. The route of administration may be orally or parenterally.

Preferably, each dosage unit will contain the active ingredient in an amount of from about 1 mg to about 500 mg most preferably from about 20 mg to about 200 mg given in a single dose or multiple divided doses.

For therapeutic use, the pharmacologically active compounds of the present invention will normally be administered as a pharmaceutical composition comprising, as the essential active ingredient, at least one such compound in the basic form or in the form of an addition salt with a pharmaceutically acceptable acid and in association with a pharmaceutical carrier therefor. Such addition salts include those mentioned above.

Other pharmacologically active compounds may in certain cases be included in the composition. It may be appropriate to combine the instant compound or compounds with anticholinergic agents such as propantheline; $H_1$ antihistamines such mepyramine, pyribenzamine, chlorpheniramine and the like; or prostanoids.

Advantageously the composition will be made up in a dosage unit form appropriate to the desired mode of administration, for example as a tablet, capsule, or injectable solution.

The compounds of the present invention may be made by reacting a suitably substituted N-cyano-3-methylisothiourea with hydroxylamine optionally followed by alkylation of the derived diaminooxadiazoles as outlined in the following reaction schemes I and II.

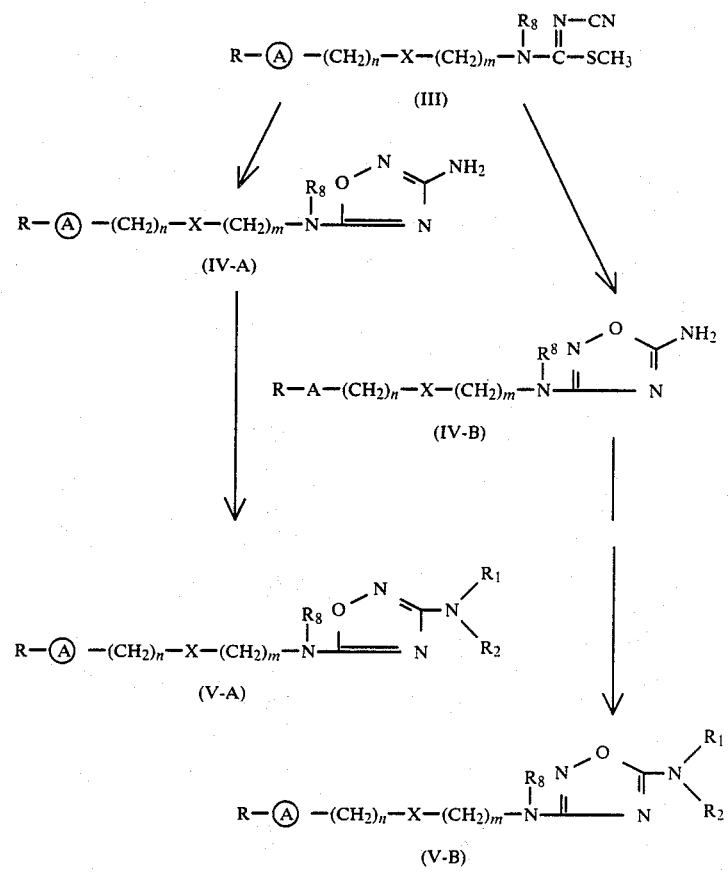

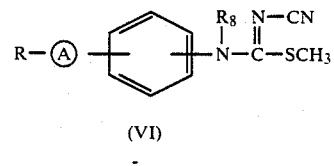

REACTION SCHEME II

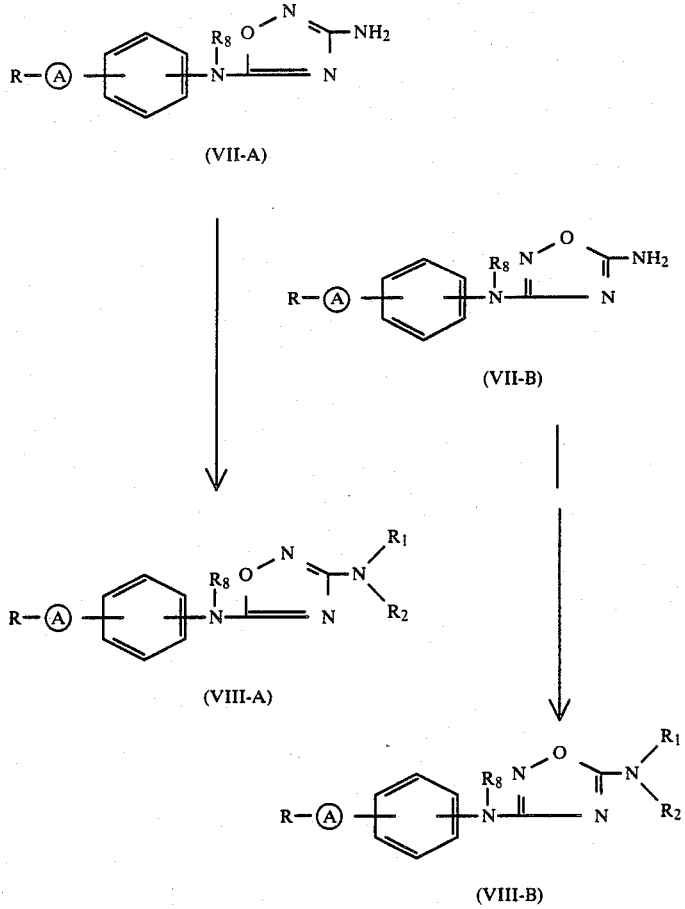

(VII-A)

(VII-B)

(VIII-A)

(VIII-B)

wherein R, (A), X, n, m, $R_1$ and $R_2$ are as previously defined.

The first step of the reaction involves the reaction of the N-cyano-S-methylisothiourea (III) with hydroxylamine. The hydroxylamine is generally added to the reaction mixture as a salt, preferably the hydrochloride salt, and the free base generated in situ. The hydroxylamine free base is liberated using a base added to the reaction mixture. Any base strong enough to remove the salt from the hydroxylamine is suitable and both organic bases such as tertiary amines and inorganic bases such as sodium acetate have been used. The preferred bases are pyridine, triethylamine, an alkali metal alkoxide such as sodium or potassium methoxides or ethoxide. The base is required to be present in a single molar equivalent, however, excess base has not been found to be detrimental.

Alternatively, the hydroxylamine free base may be pregenerated and added to the reaction mixture without any added base in the form of a solution thereof. The reaction may also be carried out using hydroxylamine salts, however, yields are diminished and variable. It is preferred to carry out the reaction with a hydroxylamine salt and to liberate the free base in situ.

The reaction is carried out in a polar or non-polar solvent and the choice of solvent somewhat determines the nature of the products obtained. If a non-polar solvent is employed, such as tetrahydrofuran, ether, benzene and the like, compound IV-A is the product formed almost exclusively. (That is the product of Formula I wherein Y is O and Z is N). If a polar solvent is used, such as a loweralkanol, preferably methanol or ethanol, a mixture of compounds IV-A and IV-B is obtained. The mixture is readily separated chromatographically using any of the generally used chromatographic techniques such as thin layer preparative layer, column, high pressure liquid chromatography and the like. The support medium may be alumina, silica gel, ion exchange resins, dextran gels and the like.

With either polar or non-polar solvents, the reaction is carried out from room temperature to the reflux temperature of the reaction medium. It is preferred to carry out the reaction at room temperature. The reaction is slow and reaction times of from 2 days to 2 weeks are not uncommon. The progress of the reaction is conveniently monitored using thin layer chromatographic analysis of an aliquot of the reaction mixture. Using this technique many reactions have been found to reach a point of no further reaction in about 4–5 days. The products are isolated using techniques known to those skilled in the art.

The products of the first step of the reaction have the unsubstituted amine function on the 3-position (IV-A) or 5-position (IV-B) of the oxadiazole moiety. The 3-amino function of IV-A when $R_8$ is other than hydrogen is substituted with the $R_1$ and $R_2$ groups by reaction with a strong base such as an alkali metal alkoxide, preferably sodium or potassium methoxide or ethoxide; or an alkali metal hydride, preferably sodium or potassium hydride. The reaction is carried out in a solvent such as N,N-dimethyl formamide or tetrahydrofuran. The alkali metal salt thus produced is then reacted with an $R_1$ or $R_2$ halide wherein $R_1$ and $R_2$ are as previously defined.

The compounds (IV-A) wherein $R_8$ is loweralkyl alkyl are prepared directly from compound III when $R_8$ is loweralkyl or from the compounds (IV-A) wherein $R_8$ is hydrogen using the same procedure as described above for the preparation of those compounds wherein $R_1$ and $R_2$ are other than hydrogen. Hydrogen atoms on the 5-nitrogen substituent of the diamino oxadiazole are more acidic than those on the 3-nitrogen substituent. Thus, such groups must be blocked with a protecting group before alkylation can be carried out on the 3-nitrogen substituent. Preferred protecting groups are aralkoxy, preferably benzyloxymethyl, prepared from the corresponding halide using conventional techniques. The conversion of IV-A to V-A requires the blocking of the internal 5-nitrogen substituent with similar protecting groups, followed by subsequent alkylation with $R_1$ or $R_2$ halides. The protecting group is removed by acid hydrolysis with aqueous acid.

The N-cyano-S-methylisothiourea starting materials are all known compounds fully described in the prior art discussed above. Thus, processes for their preparation need not be described here.

The following examples are provided in order that this invention might be more fully understood. They are not to be construed as limitative of the invention.

EXAMPLE 1

3-Amino-5-N-[2-[(5-dimethylaminomethyl-2-furanyl)-methylthio]ethyl]amino-1,2,4-oxadiazole and 5-amino-3-N-[2-[(5-dimethylaminomethyl-2-furanyl)-methylthio]ethyl]amino-1,2,4-oxadiazole A solution of 4.90 g (15.7 mmole) of N-cyano-N'-2-[5-(dimethylaminomethyl)2-furanylmethyl-thio)ethyl-S-methylisothiourea, 3.85 g (55 mmole) of hydroxylamine hydrochloride, and 7.7 ml (5.6 g, 55 mmole) of triethylamine in 15 ml of absolute methanol is stirred gently at ambient temperature for four days or until the disdisappearance of starting material by thin layer chromatography is observed. The thin layer chromatography system is alumina GF, and elution is with 95% chloroform, 5% methanol.

The reaction solution is concentrated to an oil on a film evaporator and the oil is partitioned between ethyl acetate and dilute aqueous sodium carbonate solution. Following two additional ethyl acetate extractions of the aqueous phase the combined organic layers are dried over sodium sulfate, filtered and evaporated in vacuo to an oil which is a mixture of two thin layer chromatography spots, with Rf valves of 0.62 and 0.47. The mixture is chromatographed on a column of neutral alumina (90 g, activity III), eluting with chloroform. Separation of the two components is accomplished. The major component is an oil, 900 mg with a thin layer chromatography Rf of 0.62. Mass spectral and $^{13}C$, $^1H$ NMR data confirm the structure as 3-amino-5-N-[2-[(5-dimethylaminomethyl-2-furanyl)methylthio]-ethyl-]amino-1,2,4-oxadiazole. This oil, on standing, crystallizes to a white solid, mp 88°-89° C.; this is identical with the material prepared in tetrahydrofuran (Example 2). Nuclear magnetic resonance spectroscopy of this material reveals the following characteristic peaks. Resonances were taken in CDCl$_3$ and are given in δ relative to tetramethylsilane: $^{13}C$-nuclear magnetic resonance 170.1 and 168.2 (oxadiazole carbons) $^1H$-nuclear magnetic resonance 4.55 (singlet, 2 protons from —NH$_2$) 7.46 (triplet, 1 proton from —NH).

The minor component is also an oil, 500 mg with with a thin layer chromatography Rf of 0.47. Mass spectral and $^{13}C$, $^1H$ NMR data confirm the structure 5-amino-3-N-[2-[(5-dimethylaminomethyl-2-furanyl)-methylthio]ethyl]amino-1,2,4-oxadiazole. Nuclear magnetic resonance spectroscopy of this material reveals the following characteristic peaks. Resonances were taken in CDCl$_3$ and are given in δ relative to tetramethylsilane: $^{13}C$-nuclear magnetic resonance 170.2 and 168.5 (oxadizole carbons) $^1H$ nuclear magnetic resonance 5.69 (triplet, 1 proton from —NH) 6.52 (singlet, 2 protons from —NH$_2$).

EXAMPLE 2

3-Amino-5-N-[2-[(5-dimethylaminomethyl-2-furanyl)-methylthio]ethyl]amino-1,2,4-oxadiazole A solution of N-cyano-N'-2-[5-(dimethylaminomethyl)-2-furanylmethylthio]ethyl-S-methylisothiourea (9.37 g, 0.030 mole) in 150 ml of dry tetrahydrofuran is treated with 3.00 g (0.045 mole) of hydroxylamine hydrochloride and 6.00 ml (0.045 mole) of triethylamine and stirred for 8 days at ambient temperature. The mixture is concentrated under vacuum, and the residue is partitioned between 100 ml of ethyl acetate and 50 ml of saturated sodium bicarbonate solution. 25 Ml of saturated sodium carbonate solution is added to the aqueous layer, and it is extracted with two 100 ml portions of ethyl acetate. The organic layers are combined, dried over anhydrous sodium sulfate, filtered, and concentrated under vacuum to give 10.46 g of an oil. The oil is purified by column chromatography using activity III neutral alumina. The product is contained in fractions eluted by chloroform, followed by 1% methanol and 10% methanol in chloroform. Concentration of the fractions under high vacuum affords 5.60 g of crude solid material. Recrystallization from water yields 3.26 g of 3-amino-5-N-[2-[(5-dimethyl-aminomethyl-2-furanyl)methylthio]ethyl]amino-1,2,4-oxadiazole mp 88°-89° C. The nuclear magnetic resonance spectrum of this compound is identical with the 3-amino isomer prepared in Example 1.

EXAMPLE 3A

3-Amino-5-[N-methyl-N-[2-[(5-dimethylaminomethyl-2-furanyl)methylthio]ethyl]amino-1,2,4-oxadiazole A mixture of 3-amino-5-N-[2-(5-dimethylaminomethyl)-2-furanylmethylthio]ethylamino-1,2,4-oxadiazole (1.5 g, 5.0 mmole) and 250 mg (5.0 mmole) of a 50% sodium hydride dispersion in 3 ml of N,N-dimethylformamide is rapidly agitated with mechanical stirring and warming under a nitrogen atmosphere. Hydrogen gas evolution and formation of a deep red solution are immediately noted after which the mixture is stirred at ambient temperature for an additional 15 minutes. Methyl iodide (0.32 ml, 5.0 mmole) is introduced via a syringe through a rubber septum and stirring of the resulting tan suspension is continued for 15 minutes. The mixture is diluted with 20 ml of water and the aqueous solution extracted with methylene chloride (3×10 ml). The combined organic extracts are extracted with two 10 ml portions of 1N hydrochloric acid and the combined aqueous acidic phases are then washed with methylene chloride before basification with solid sodium carbonate. Methylene chloride extraction of the alkaline aqueous phase gives 1.8 g of an orange oil which is purified by chromatography through a neutral alumina (activity III) column, elution with methylene chloride followed by 2% methanol in methylene chloride. Concentration of the fractions gives 1.6 g of 3-amino-5-[N-methyl-N-[2-[(5-dimethylaminomethyl-2-furanyl)methylthio]ethyl]amino]-1,2,4-oxadiazole.

EXAMPLE 3B 3-(2-Guanidino-4-thiazolyl)-N-methyl benzeneamine

A mixture of 9.3 g (0.04 mole) of 3-(2-guanidino-4-thiazolyl)benzeneamine, 20 ml of triethylorthoformate, and 2 drops of trifluoroacetic acid is stirred at reflux for 5 hours after which it is concentrated in vacuo. The residue is dissolved in 20 ml of ethanol, the solution cooled to 0° C. and then treated with excess sodium borohydride. The mixture is allowed to warm to room temperature, then stirred at reflux for 4 hours. Upon concentration in vacuo the residue is partitioned between water and dichloromethane.

After three extractions of the aqueous phase the combined dichloromethane extracts are dried over sodium sulfate and evaporated to give 3-(2-guandidino-4-thiazolyl)-N-methyl benzeneamine.

EXAMPLE 3C

N-Cyano-N'-methyl-N'-3(2-guanidino-4-thiazolyl)phenyl-S-methyl isothiourea

A solution of 5.2 g (0.021 mole) of 3-(2-guanidino-4-thiazolyl)-N-methylbenzeneamine and 3.1 g (0.021 mole) of dimethylcyanodithioimidocarbonate in 100 ml of isopropanol is gently stirred under nitrogen for 18 hours. After evaporation of the solvent, the residue is chromatographed using activity II neutral alumina and the product-containing fractions, eluted with dichloromethane, are combined. Upon removal of the solvent there is obtained 6.1 g of N-cyano-N'-methyl-N'-3(guanidino-4-thiazolyl)-phenyl-S-methylisothiourea.

EXAMPLE 3D

N-Methylamino-5N-[3-(2-quanidino-4-thiazolyl)-phenyl]amino-1,2,4-oxadiazole

Sodium hydride (0.24 g, 50% oil dispersion) (0.0050 mole) is suspended in 10 ml of dry dimethylformamide. The mixture is stirred under nitrogen, and then treated with 1.57 g (0.0050 mole) of 3-amino-5N-[3-(2-guanidino-4-thiazolyl)phenyl]amino-1,2,4-oxadiazole. After two hours, 0.080 ml (0.0055 mole) of chloromethylpoivalate is added and the resultant mixture stirred at ambient temperature for 18 hours. The mixture is cooled to 10° C., treated with additional sodium hydride (0.24 g, 50% oil dispersion) (0.0050 mole) and allowed to stir at 25° C. for 3 hours. Iodomethane (0.32 ml, 0.0050 mole) is added and vigorous stirring is continued for one hour after which time 6 ml of a 4M sodium hydroxide solution is added dropwise. The mixture is stirred at 25° C. for 5 minutes and then poured into excess aqueous sodium bicarbonate. Extractions with dichloromethane provide 3-methylamino-5N-[3-(2-guanidino-4-thiazolyl)-phenyl]-amino-1,2,4-oxadiazole as an oil.

EXAMPLE 4

3-Amino-5-N-[3-(2-guanidino-4-thiazolyl)phenyl]amino-1,2,4-oxadiazole

To a suspension of 3.31 g (0.0100 mole) of N-cyano N'-3-(2-guanidino-4-thiazolyl)phenyl-S-methylisothiourea in 50 ml dry tetrahydrofuran is added 1.04 g (0.0150 mole) of hydroxylamine hydrochloride and 1.52 g (0.0150 mole) of triethylamine. The mixture is then heated at reflux for 21 hours, at which time no further change is noted by thin layer chromatography. The solution is concentrated to dryness in vacuo, and the residue is washed with 50 ml of saturated sodium bicarbonate solution and 50 ml of ethyl acetate and 30 dried to give 2.41 g (77%) of crude product.

The crude product is placed in 5 ml of water and 7.7 ml of 1N hydrochloric acid is added. The solution is filtered and concentrated in vacuo until a precipitated begins to form. Additional water is then added until the solid dissolves. Addition of acetonitrile to the aqueous solution causes precipitation of the product. 1.12 G of the hydrochloride salt is obtained.

The hydrochloride salt is dissolved in 5 ml of water and basified with concentrated ammonia to give 0.90 g of material containing product and origin material according to thin layer chromatography. The material is eluted through a small pad of E. Merck silica gel 60 by a solution of 20% methanol 80% chloroform. The material obtained is then dissolved in 1 ml of dimethylsulfoxide and precipitated by the addition of water to give 0.41 g (13%) of product, m.p. 240°–242°, thin layer chromatography (20% methanol 80% chloroform, silica gel) Rf 0.2.

Following the foregoing procedures, the listed N-cyano-S-methylisothiourea intermediates are prepared from the amine reactant and dimethylcyanodithioimidocarbonate. Reaction of such intermediates with hydroxylaamine affords the oxadiazoles.

Typical compounds encompassed by this invention include:

| Oxadiazole | Oxadiazole Precursor | Amine Reactant |
| --- | --- | --- |
| 3-Methylamino-5N—[2-[(5-dimethylamino-methyl-2-furanyl)-methylthio]ethyl]-amino-1,2,4-oxadiazole | 3-Amino-5N-[2-[(5-dimethyl-aminomethyl-2-furanyl)-methylthio]ethyl]-amino-1,2,4-oxadiazole* | 2-[(5-Dimethylamino-methyl-2-furanyl)methyl-thio]ethylamine |
| 5-Amino-3-[N—methyl-N—[2-[(5-dimethyl-aminomethyl-2-furanyl)methylthio]-ethyl]amino-1,2,4-oxadiazole | N—Cyano-N'—methyl-N'—[2-[(5-dimethylaminomethyl-2-furanyl)methylthio]-ethyl]-S—methylisothiourea | N—Methyl-N—[2-[(5-Dimethyl-2-furanyl)-methylthio]methylethyl]-amine |
| 3-Amino-5N—[2-[(5-guanidino-4-thia-zolyl)-methylthio]-ethyl]amino-1,2,4- | N—Cyano-N'—2-[(2-guanidino-4-thiazolyl)methylthio]-ethyl-S—methylisothiourea | 2-[(Guanidino-4-thiazo-lyl)methylthio]ethyl-amine |

-continued

| Oxadiazole | Oxadiazole Precursor | Amine Reactant |
|---|---|---|
| oxadiazole | | |
| 3-Amino-5N—[2-[(6-(4-morpholinomethyl)-2-benzofuranyl)methylthio]ethyl]amino-1,2,4-oxadiazole | N—Cyano-N'—2-[(6-(4-morpholinomethyl)-2-benzofuranyl)methylthio]ethyl-S—methylisothiourea | 2-[(6-(4-Morpholinomethyl)-2-benzofuranyl)-methylthio]ethylamine |
| 3-Amino-5N—[3-[3-(4-morpholinomethyl)-phenoxy]propyl]-amino-1,2,4-oxadiazole | N—Cyano-N'—3-[3-(4-morpholinomethyl)phenoxy[propyl-S—methylisothiourea | 3-[3-(4-Morpholinomethyl)phenoxy]propaneamine |
| 5-Amino-3N—[3-[3-(1-piperidinomethyl)-phenoxy]propyl]amino-1,2,4-oxadiazole | N—Cyano-N'—3-[3-(1-piperidinomethyl)phenoxy]propyl-S—methylisothiourea | 3-[3-(1-Piperidinomethyl)phenoxy]propaneamine |
| 3-Amino-5N—[2-[(5-methyl-4-imidazolyl)-methylthio]ethyl]-amino-1,2,4-oxadiazole | N—Cyano-N'—2-[5-methyl-4-imidazolyl)methylthio]-ethyl-S—methylisothiourea | 2-[(5-Methyl-4-imidazolyl)methylthio]-ethylamine |
| 3-Amino-3N—[2-[(5-methyl-4-imidazolyl)-methylthio]ethyl]-amino-1,2,4-oxadiazole | N—Cyano-N'—2-[5-methyl-4-imidazolyl)methylthio]-ethyl-S—methylisothiourea | 2-[(5-Methyl-4-imidazolyl)methylthio]-ethylamine |
| 3-Amino-5N—[2-[(6-dimethylaminomethyl-2-pyridyl)methylthio]-ethyl]amino-1,2,4-oxadiazole | N—Cyano-N'—2-[(6-dimethylaminomethyl-2-pyridyl)-methylthio]ethyl-S—methylisothiourea | 2-[(6-Dimethylaminomethyl-2-pyridyl)methylthio]ethylamine |
| 5-Amino-3N—[[3-2-guanidino-4-thiazolyl)phenyl]-N—methyl]amino-1,2,4-oxadiazole | N—Cyano-N'—methyl-N'-3-(2-guanidino-4-thiazolyl)-phenyl-S—methylisothiourea | 3-(2-Guanidino-4-thiazolyl)-N—methylbenzeneamine |

*Subjected to successive alkylative blocking of 5N—, alkylation of 3N—, then deblocking of 5N.

EXAMPLE 14

N-2-[5-Dimethylaminomethyl-2-furanyl)methylthio]ethylcyanamide

2-[5-Dimethylaminomethyl-2-furanyl)methylthio]ethylamine (21.4 g, 0.10 mole) and hexamethyldisilazane (30 g) are combined and refluxed vigorously under nitrogen for 18 hours. The resulting mixture is distilled in vacuo to give N-trimethylsilyl-2-[(5-dimethylaminomethyl-2-furanyl)-methylthio]ethyl amine, bp 95°–96° (0.1 mm) as a clear colorless liquid.

This compound (14.4 g, 0.050 mol) is dissolved in 100 ml of methylene chloride at −20° C. under nitrogen and the stirred solution treated dropwise with a solution of cyanogen bromide (5.3 g, 0.05 mole) in 50 ml of methylene chloride. The resulting solution is stirred for one hour at −20° C. then concentrated in vacuo at 10°–20° C. to give crude N-2-[5-Dimethylaminomethyl-2-furanyl)methylthio]ethylcyanamide.

EXAMPLE 15

2-Hydroxy-1-[2-[(5-dimethylaminomethyl-2-furanyl)-methyl-thio]ethyl quanidine

The cyanamide from Example 14 (9.56 g, 40 mmol) is added to a stirred suspension of hydroxylamine hydrochloride (4.0 g, 58 mmol) and sodium acetate trihydrate (8.2 g, 60 mmol) in 400 ml of N,N-dimethylformamide. The mixture is stirred overnight at 60° C. under nitrogen. The mixture is diluted with water and extracted with ethyl acetate. The extracts are combined and washed with saturated aqueous sodium chloride solution and dried over anhydrous potassium carbonate. Concentration of the filtered ethyl acetate solution in vacuo gives crude 2-Hydroxy-1-[2-[(5-dimethylaminomethyl-2-furanyl)methylthiol]ethyl guanidine

EXAMPLE 16

3-[2-[(5-Dimethylaminomethyl-2-furanyl)methylthio]ethyl]-amino-5-trichloromethyl-1,2,4-oxadiazole The guanidine from Example 15 (5 g, 18 mmol) is dissolved in 75 ml of tetrahydrofuran at 0° C. and the solution treated dropwise with trichloroacetic anhydride (3.7 g, 20 mmol). The mixture is warmed to room temperature overnight under an atmosphere of dry nitrogen. Most of the solvent is removed in vacuo and the residue is partitioned between aqueous sodium carbonate and methylene chloride. The methylene chloride extract is dried over sodium sulfate, filtered and concentrated in vacuo to an oil which is chromatographed on silica gel to give pure 3-[2-[(5-Dimethylaminomethyl-2-furanyl)methylthio]-ethyl]-amino-5-trichloromethyl-1,2,4-oxadiazole.

EXAMPLE 17

2-[2-[(5-Dimethylaminomethyl-2-furanyl)methylthio]ethyl]amino-5-methylamino-1,2,4-oxadiazole The oxadiazole from Example 16 (3 g, 7.5 mmol) is dissolved in 25 ml of ethanol saturated with methylamine and the solution heated in a sealed tube at 50° C. for 16 hours. The mixture is concentrated to provide 3-[2-[(5-Dimethylaminomethyl-2-furanyl)methylthio]ethyl]-amino-5-methylamino-1,2,4-oxadiazole as an oil.

EXAMPLE 18

Antisecretory Activity Tests

3-Amino-5-N[2[(5-dimethylaminomethyl-2-furanyl)-methylthio]ethyl]-amino-1,2,4-oxadiazole (Compound A) and 5-amino-3-N[2-[(5-dimethylamino-methyl-2-furanyl)methylthio]ethyl]amino-1,2,4-oxadiazole (Compound B), prepared according to Example 1, and 3- amino-5-N-[3-(2-guanidino-4-thiazolyl)phenyl]amino-1,2,4-oxadiazole (Compound C), prepared according to Example 4, which compounds are representative of the compounds according to the instant invention, were submitted for testing in fistula dogs against gastric histamine stimulation, according to the method described in W. A. Bolhofer et al., *J. Med. Chem.*, 22, 301 (1979).

The test results:

| Compound | Inhibition Volume (%) | Inhibition Acid (%) | i.v. dose Amount (mg/kg) |
|---|---|---|---|
| A | max. 55 | 64 | 2.5 |
| B | max. 51 | 57 | ca. 4.1 |
| C | max. 53 | 22 | 0.3 | clearly show these compounds to have utility as antisecretory agents.

What is claimed is:

1. A compound having the formula:

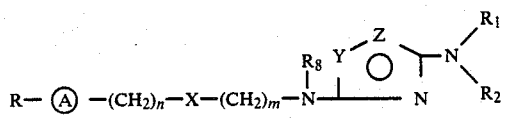

wherein R is hydrogen, loweralkyl,

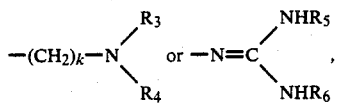

wherein
$R_3$ and $R_4$ are independently hydrogen, lower-alkyl, cycloloweralkyl, or phenylloweralkyl, or $R_3$ and $R_4$ may be joined to form, along with the nitrogen to which they are attached, a nonaromatic one- or two-heteroatom-5-membered heterocycle, the heteroatom of the one-heteroatom-5-membered heterocycle being said nitrogen atom, and the heteroatoms of the two-heteroatom-5-membered heterocycle consisting of said nitrogen atom and an oxygen atom, a sulfur atom or an N-$R_7$ group, wherein $R_7$ is hydrogen, $C_1$-$C_3$-alkyl or benzyl;
$R_5$ and $R_6$ are independently hydrogen or loweralkyl;
n is 0 or 1;
m is 2, 3 or 4;
k is 1, 2, 3 or 4;
X is oxygen, sulfur or methylene;
Y and Z are different, and are either oxygen or nitrogen;
$R_1$ and $R_2$ are independently hydrogen; lower-alkyl; substituted loweralkyl, wherein the substituent is phenyl, or imidazolyl; loweralkenyl; lower-alkynyl; or loweralkanoyl;
$R_8$ is hydrogen or loweralkyl; and
(A) is phenylene; a 5-membered aromatic heterocycle having one-to-three heteroatoms in addition to the carbon atoms in the ring, wherein each heteroatom is selected from oxygen, sulfur or nitrogen; or a 5-membered aromatic heterocycle having a benzo ring fused thereon, where the heterocycle has one-to-three heteroatoms in addition to the carbon atoms in the ring, wherein each heteroatom is selected from oxygen, sulfur or nitrogen;

and physiologically-acceptable salts thereof.

2. A compound according to claim 1, wherein $R_1$ and $R_2$ are independently hydrogen, $C_1$- or $C_2$-alkyl, or $C_2$- or $C_3$-alkynyl; m is 2 or 3; $R_8$ is hydrogen and X is oxygen or sulfur.

3. A compound according to claim 2, wherein X is sulfur, n is one, (A) is an aromatic one-heteroatom 5-membered heterocycle, the single heteroatom of which is an oxygen or sulfur atom, or a one-heteroatom-benzofused-5-membered-heterocycle, the single heteroatom of which is an oxygen or sulfur atom, and R is

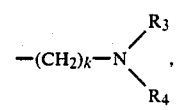

wherein k is one, and $R_3$ and $R_4$ are independently hydrogen or $C_1$-$C_5$-alkyl or $R_3$ and $R_4$ are joined with the nitrogen to form a nonaromatic one-heteroatom-5-membered heterocycle.

4. A compound according to claim 2, wherein X is sulfur, m is two, n is one, (A) is an aromatic two-heteroatom-5-membered-heterocycle, one heteroatom of which is nitrogen, and R is

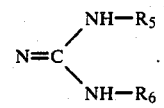

5. A compound according to claim 2, wherein X is sulfur, n is one, (A) is an aromatic three-heteroatom-5-membered-heterocycle, at least one heteroatom of which is nitrogen, and R is

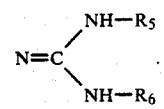

6. A compound according to claim 2, wherein X is sulfur, m is two, n is one, (A) is an aromatic two-heteroatom-5-membered-heterocycle, the two heteroatoms of which are nitrogen atoms, and R is hydrogen or methyl.

7. The compound of claim 3, which is 3-amino-5-N-[2-[(5-dimethylaminomethyl-2-furanyl)-methylthio]ethyl]amino-1,2,4-oxadiazole.

8. The compound of claim 3, which is 5-amino-3-N-[2-[(5-dimethylaminomethyl-2-furanyl)-methylthio]ethyl]amino-1,2,4-oxadiazole.

9. The compound according to claim 4, which is 3-amino-5-N-[3-(2-guanidino-4-thiazolyl)-methylthioethyl]amino-1,2,4-oxadiazole.

10. A compound having the formula:

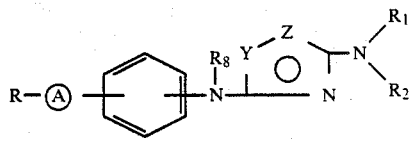

wherein
R is hydrogen, loweralkyl,

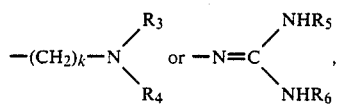

wherein R₃ and R₄ are independently hydrogen, loweralkyl, cycloloweralkyl, or phenylloweralkyl, or R₃ and R₄ may be joined to form, along with the nitrogen to which they are attached, a nonaromatic one- or two-heteroatom-5-membered heterocycle, the heteratom of the one-heteroatom-5-membered heterocycle being said nitrogen atom, and the heteroatoms of the two-heteroatom-5-membered heterocycle consisting of said nitrogen atom and an oxygen atom, a sulfur atom or an N-R₇ group, where R₇ is hydrogen, $C_1$–$C_3$-alkyl or benzyl;

R₅ and R₆ are independently hydrogen or loweralkyl;

k is 1, 2, 3 or 4;

Y and Z are different, and are either oxygen or nitrogen;

R₁ and R₂ are independently hydrogen; lower-alkyl; substituted lower alkyl, where the substituent is phenyl, or imidazolyl; loweralkenyl; lower-alkynyl; or loweralkanoyl;

R₈ is hydrogen or loweralkyl; and

Ⓐ is phenylene; a 5-membered aromatic heterocycle having one to three heteroatoms in addition to the carbon atoms in the ring, wherein each heteroatom is selected from oxygen, sulfur or nitrogen; or a 5-membered aromatic heterocycle having a benzo ring fused thereon, where the heterocycle has one-to-three heteroatoms in addition to the carbon atoms in the ring, wherein each heteroatom is selected from oxygen, sulfur or nitrogen.

11. A compound according to claim 10, wherein R₁ and R₂ are independently hydrogen, $C_1$- or $C_2$-alkyl, or $C_2$- or $C_3$-alkynyl; and R₈ is hydrogen.

12. A compound according to claim 11, wherein Ⓐ is an aromatic one-heteroatom-5-membered-heterocycle, the single heteroatom of which is an oxygen or sulfur atom, or a one-heteroatom-benzofused-5-membered-heterocycle, the single heteroatom of which is an oxygen of suflur atom, and R is

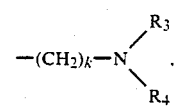

where k is one, and R₃ and R₄ are independently hydrogen or $C_1$–$C_5$-alkyl or R₃ and R₄ are joined with the nitrogen to form a nonaromatic one-heteroatom-5-membered heterocycle.

13. A compound according to claim 11, wherein Ⓐ is an aromatic two-heteroatom-5-membered-heterocycle, one heteroatom of which is nitrogen, and R is

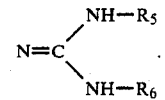

14. A compound according to claim 11, wherein Ⓐ is an aromatic three-heteroatom-5-membered-heterocycle, at least one heteroatom of which is nitrogen, and R is

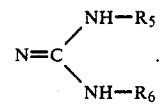

15. A compound according to claim 11, wherein X is sulfur, n is one, Ⓐ is an aromatic two-heteroatom-5-membered-heretocycle, the two heteroatoms of which are nitrogen atoms, and R is hydrogen or methyl.

16. The compound according to claim 13, which is 3-amino-5-N-[3-(2-guanidino-4-thiazolyl)phenyl]amino-1,2,4-oxadiazole.

17. A method of suppressing excess gastric acid secretions in an animal which comprises administering to said animal a pharmaceutically-effective amount of a compound according to claim 1.

18. A composition useful for suppressing excess gastric acid secretions in an animal which comprises an inert carrier and a pharmaceutically-effective amount of a compound according to claim 1.

19. A method for suppressing excess gastric acid secretions in an animal which comprises administering to said animal a pharmaceutically-effective amount of a compound according to claim 10.

20. A composition useful for suppressing excess excess gastric acid secretions in an animal which comprises an inert carrier and a pharmaceutically-effective amount of a compound according to claim 10.

* * * * *